(12) United States Patent
Spangenberg et al.

(10) Patent No.: US 10,051,777 B2
(45) Date of Patent: Aug. 21, 2018

(54) METHOD FOR LARGE SCALE GENERATION OF ARTIFICIAL SEEDS COMPRISING SYMBIOTA

(71) Applicant: Agriculture Victoria Services PTY LTD, Attwood, Victoria (AU)

(72) Inventors: German Carlos Spangenberg, Bundoora (AU); Yidong Ran, Bundoora (AU); John Gregory Mason, Preston (AU); Kathryn Michaela Guthridge, Hadfield (AU)

(73) Assignee: Agriculture Victoria Services Pty Ltd, Attwood (AU)

( * ) Notice: Subject to any disclaimer, the term of this patent is extended or adjusted under 35 U.S.C. 154(b) by 457 days.

(21) Appl. No.: 14/404,856

(22) PCT Filed: May 29, 2013

(86) PCT No.: PCT/AU2013/000558
§ 371 (c)(1),
(2) Date: Dec. 1, 2014

(87) PCT Pub. No.: WO2013/177616
PCT Pub. Date: Dec. 5, 2013

(65) Prior Publication Data
US 2015/0150161 A1    May 28, 2015

(30) Foreign Application Priority Data

Jun. 1, 2012 (AU) .............................. 2012902278
Sep. 7, 2012 (AU) .............................. 2012903895

(51) Int. Cl.
*A01C 1/06* (2006.01)
*A01H 17/00* (2006.01)
(Continued)

(52) U.S. Cl.
CPC ............... *A01C 1/06* (2013.01); *A01H 4/006* (2013.01); *A01H 5/10* (2013.01); *A01H 5/12* (2013.01); *A01H 17/00* (2013.01); *Y02A 40/15* (2018.01)

(58) Field of Classification Search
CPC ............. A01C 1/06; A01H 4/006; A01G 1/00
(Continued)

(56) References Cited

U.S. PATENT DOCUMENTS

| 4,251,952 A * | 2/1981 | Porter ..................... A01C 1/06 |
| | | 47/57.6 |
| 5,427,593 A | 6/1995 | Carlson et al. |

(Continued)

FOREIGN PATENT DOCUMENTS

| CN | 1843096 A | 10/2006 |
| EP | 0 107 141 B1 | 2/1988 |

(Continued)

OTHER PUBLICATIONS

D.G. Strullu et al.; Mycorrhizal synthesis in vitro between *Glomus* spp. and artificial seeds of alfalfa; New Phytologist; Dec. 1989; 113; 545-548.*

(Continued)

*Primary Examiner* — Kent L Bell
(74) *Attorney, Agent, or Firm* — Larson & Anderson, LLC

(57) ABSTRACT

The present invention relates to new methods of selecting and breeding organisms, in particular organisms which exhibit symbiotic behavior with symbionts such as fungal endophytes or epiphytes or bacterial microbiome in plants, and to new organisms and symbiota developed thereby. More particularly, the present invention provides artificial seeds comprising symbiota, and methods for preparing and using such artificial seeds, as well as plants, plant seeds and other plant parts derived from artificial seeds or symbiont-containing plants of the present invention.

8 Claims, 8 Drawing Sheets

(51) Int. Cl.
*A01H 4/00* (2006.01)
*A01H 5/10* (2018.01)
*A01H 5/12* (2018.01)

(58) Field of Classification Search
USPC .......................................... 800/298; 47/57.6
See application file for complete search history.

(56) References Cited

U.S. PATENT DOCUMENTS

| | | | | |
|---|---|---|---|---|
| 6,164,012 | A | * | 12/2000 | Lechelt-Kunze ...... A01H 4/001 47/57.6 |
| 2003/0195117 | A1 | | 10/2003 | Imada et al. |
| 2012/0144533 | A1 | | 6/2012 | Craven |

FOREIGN PATENT DOCUMENTS

| | | |
|---|---|---|
| EP | 0 192 342 B1 | 2/1992 |
| EP | 0192342 | 2/1992 |
| JP | 03-155722 | 7/1991 |
| JP | 03155722 | 7/1991 |
| JP | H03-155722 A | 7/1991 |
| JP | H06-502535 | 3/1994 |
| JP | 07274723 A | 10/1995 |
| JP | 2002-209441 | 7/2002 |
| JP | 2003-300805 | 10/2003 |
| JP | 2006-174811 A | 7/2006 |
| JP | 2006-328033 A | 7/2006 |
| WO | 92/07457 A1 | 5/1992 |
| WO | 2000/062600 A1 | 10/2000 |
| WO | 02/13616 A2 | 2/2002 |

OTHER PUBLICATIONS

Cangahuala-Inocente, G. et al. "Improvements in somatic embryogenesis protocol in Feijoa (Acca sellowiana (Berg) Burret): Induction, conversion and synthetic seeds", Scientia Horticulturae, 2007, pp. 228-234, vol. 111.

Fujii, J. et al. "Alfalfa somatic embryo maturation and conversion to plants" Plant Science, 1990, pp. 93-100, vol. 72.

Onishi, N. et al. "Synthetic seeds as an application of mass production of somatic embryos" Plant Cell, Tissue & Organ Culture, 1994, pp. 137-145, vol. 39.

Ownley, B. et al. "Beauveria bassiana: Endophytic colonization and plant disease control", Journal of Invertebrate Pathology, 2008, pp. 267-270, vol. 98.

Schardl, C. et al. "Symbioses of Grasses with Seedborne Fungal Endophytes", Annual Rev. Plant Biol. 2004, pp. 315-340, vol. 55.

English translation of Japanese Office Action dated Feb. 20, 2017 from corresponding Japanese Patent Application No. 2015-514287, 10 pages.

Azcon-Aguilar, C. et al. "Applying mycorrhiza biotechnology to horticulture: significance and potentials", Scientia Horticulture, 1997, pp. 1-24, vol. 68.

Jha, P.K. et al. "Encapsulation of seeds of Sesbania sesban with polyacrylamide and alginate gel entrapped rhizobia leads to effective symbiotic nitrogen fixation" Indian Journal of Experimental Botany, 1993, pp. 161-167, vol. 31.

My Agriculture Information Bank "Importance of artificial seeds" AgriInfo.in, 2011, retrieved from internet on Aug. 23, 2013.

Saiprasad, G.V.S. "Artificialseeds and their applications" Resonance, 2001, pp. 39-47, vol. 6.

Wood, C.B. et al. "Simultaneous preservation of orchid seed and its fungal symbiont using encapsulation-dehydration is dependent on moisture content and storage temperature" CyroLetters, 2000, pp. 125-136, vol. 21.

Zhang, M. et al. "Preparation technique of Cremastra appendiculata synthetic seed" China Journal of Chinese Materia Medica, 2009, pp. 1894-1897, vol. 34.

First Office Action dated Jan. 12, 2016 from corresponding Chinese Patent Application No. 2013800411394.

Takemoto, et al. "Mycotoxins" 2011, pp. 13-18, vol. 61, No. 1—English Abstract included.

Biology and Chemistry (1985) vol. 23, No. 2, pp. 103-111. Japanese language document; concise explanation of relevance attached.

* cited by examiner

METHOD FOR LARGE SCALE GENERATION OF ARTIFICIAL SEEDS COMPRISING SYMBIOTA

FIELD OF THE INVENTION

The present invention relates to new methods of selecting and breeding organisms, in particular organisms which exhibit symbiotic behaviour with symbionts such as fungal endophytes or epiphytes or bacterial microbiome in plants, and to new organisms and symbiota developed thereby.

BACKGROUND OF THE INVENTION

The phenotype of many species of livestock, crops and pastures depends on the interaction between the genotype of the individual and the genotype of a symbiont. Important plants, including forage grasses, legumes, trees, shrubs, and vines are commonly found in association with endophytes including fungi, bacteria, viruses and microbes. Similarly, important animals, including cattle, sheep, pigs, goats, etc. have such endophytes present in their gut and rumen.

Both beneficial and detrimental horticultural, agronomic and veterinary properties result from such associations, including improved tolerance to water and nutrient stress and resistance to insect pests.

For example, ryegrass plants can show improved drought tolerance and persistency if a fungal endophyte of the correct genotype colonises the plant. Similarly, in grasses, insect resistance may be provided by specific metabolites produced by the endophyte, in particular loline alkaloids and peramine. Other metabolites produced by the fungal endophyte, for example lolitrems and ergot alkaloids, may be toxic to grazing animals and reduce herbivore feeding.

Considerable variation is known to exist in the metabolite profile of symbionts such as endophytes. For example, fungal endophyte strains that lack either or both of the animal toxins have been introduced into commercial ryegrass varieties.

In animals, the microorganisms present in the gut are responsible for digestion of an animal's feed. Rumen microbes-bovine symbiota may be important, for example, in improving feed conversion efficiency and reducing methane production. In ruminants, successful digestion of poor quality feed may depend on having a particular rumen microbiome profile.

Molecular genetic markers such as simple sequence repeat (SSR) markers have been developed as diagnostic tests to distinguish between symbiont taxa and detect genetic variation within taxa. The markers may be used to discriminate symbiont strains with different toxin profiles.

However, there remains a need for methods of identifying, isolating and/or characterising organisms which exhibit symbiotic behaviour with symbionts such as endophytes. Difficulties in artificially breeding of these symbiota limit their usefulness. For example, many of the novel endophytes known to be beneficial to pasture-based agriculture exhibit low inoculation frequencies and are less stable in elite germplasm.

Moreover, in traditional breeding techniques, for example in forage grasses such as perennial ryegrass and tall fescue, grass varieties are bred using classic cross-breeding techniques and grass genotypes are selected for their superior characteristics, after monitoring their performance over a period of multiple years. The selected grass genotypes that form the experimental variety are then inoculated with a single endophyte and the resulting grass-endophyte associations are evaluated for any favourable characteristics such as insect resistance. The individual experimental synthetic varieties deploying a single endophyte in them are then evaluated for agronomic performance and resulting animal performance by grazing animals over a period of years. This evaluation process may reveal that the single endophyte being deployed in the different experimental synthetic varieties may not show vegetative and/or intergenerational stability in some of these varieties or the desired alkaloid profile conferred by the single endophyte may vary between different synthetic varieties failing to confer appropriate levels of insect resistance or causing animal toxicoses. It would be a significant development in the art if this time-consuming process could be accelerated or otherwise improved.

It is accordingly an object of the present invention to overcome, or at least alleviate, one or more of the difficulties or deficiencies associated with the prior art.

SUMMARY OF THE INVENTION

United States patent applications filed 1 Jun. 2012 and 7 Sep. 2012, entitled 'Novel Organisms', the entire disclosures of which are incorporated herein by reference, describe methods of deploying multiple symbionts in multiple organisms and to select for improved symbiotic compatibility and performance early in the breeding process. That is symbiont-organism genotype combinations are bred and screened for desired characteristics including improved symbiota compatibility and performance ab initio. To facilitate this, applicants have developed methods for large-scale establishment of symbiota through artificial seed production and inoculation methods.

Accordingly, in a first aspect of the present invention, there is provided a method for preparing artificial seeds which method includes:
   providing a source of plant seeds;
   subjecting the seed(s) to a surface-sterilisation step;
   isolating seed embryo(s) from the surface-sterilised seed(s); and
   coating the embryo(s) with a coating to form artificial seed(s).

The seeds may be from any suitable plant. The plant may be a grass, preferably a perennial grass, legume, vine, shrub, tree, herb, flower, shrub or bush. The method according to this aspect of the present invention is particularly applicable to grasses and legumes.

The seeds may be surface-sterilised by any suitable technique. Preferably the seeds are sterilised by treating them with an acid such as hydrochloric acid and bleach, such as sodium hypochlorite. Preferably the acid and bleach treatments are performed sequentially. The acid treatment may be for a period of from 1 hour to 24 hours, preferably overnight. The bleach treatment may be for a period of 5 minutes to 1 hour, preferably approximately 20 minutes. The bleach treatment may be performed twice on successive days, with the seeds being washed after each treatment, for example using sterile distilled water, and stored at approximately 4 to 30° C., preferably approximately 24° C.

Embryos may be isolated from the treated seeds by techniques known to those skilled in the art.

In a preferred embodiment, the embryos may be treated to create one or more points of entry for the symbiont, e.g. endophyte. For example, the embryo may be punctured or its surface otherwise damaged, for example by scratching or etching, to facilitate entry of the symbiont. In a particularly preferred embodiment, a hypodermic needle or similar may be used to create single or multiple puncture holes in the surface of the embryo.

The coating may be of any suitable type to encapsulate the embryo, including alginate, agar, polyco 2133, carboxy methyl cellulose, carrageenan, gelrite, guargum, sodium pectate, tragacanth gum and the like. In a preferred embodiment the coating is alginate, more particularly calcium alginate.

In a preferred embodiment, the embryos may be mixed with the coating and drops of coating containing individual embryos placed in a polymerising solution such as calcium chloride solution, preferably while stirring, to form artificial seeds. Artificial seeds may be collected following approximately 1-60 minutes stirring, preferably after approximately 15 minutes stirring.

In a preferred embodiment the embryos may be inoculated with a symbiont such as a fungal endophyte prior to coating. In a preferred form, the embryos may be directly inoculated with endophyte mycelium.

Alternatively, in a particularly preferred embodiment, isolated embryos may be coated with a symbiont-containing coating layer, such as a fungal endophyte-containing coating layer.

In this embodiment, the inoculation step may include:
providing a source of seed embryos;
inoculating the embryos with one or more symbionts such as fungal endophytes; and
coating the inoculated embryo(s) with a coating to form artificial seed(s).
Alternatively, the inoculation step may include:
providing a source of seed embryos; and
coating the embryos with a coating containing symbionts such as fungal endophytes to form artificial seed(s).

In a preferred embodiment the seeds may be double coated with a second coating layer. Preferably the second coating layer is alginate, more preferably calcium alginate, even more preferably coloured calcium alginate. In a preferred embodiment, the artificial seeds with the first coating layer may be air dried prior to coating with the second layer.

In a preferred embodiment, the method may further include coating the artificial seeds with a second coating layer, said second coating layer preferably containing added nutrients suitable for sustaining the embryo and/or symbiont.

Alternatively, the second coating layer may not contain added nutrients, this nutrient deprived layer being designed to, for example, reduce endophyte out-growth during germination and restrict endophyte growth in close proximity to the embryo.

In another aspect of the present invention, there is provided an artificial seed selected from the group consisting of:
(a) a plant embryo inoculated with one or more symbionts and coated with a coating to encapsulate the embryo; and
(b) a plant embryo coated with a symbiont-containing coating layer.

Preferably, the artificial seed is double coated with a second coating layer. The second coating layer may include added nutrients or may be a nutrient deprived layer, as described herein.

Preferably, the embryo is from a plant selected from the group consisting of grasses and legumes. Preferably it is isolated by techniques as hereinbefore described.

Preferably, the embryo is treated to create one or more points of entry for the symbiont.

In a particularly preferred embodiment symbiont may be a fungal endophyte.

In another particularly preferred embodiment, the artificial seed may be produced by a method as hereinbefore described.

In a preferred embodiment, the method of the present invention may further include
growing the artificial seeds to form plantlets or seedlings; and
screening the plantlets or seedlings for symbiont presence such as fungal endophyte presence.

The step of growing the artificial seeds may be undertaken using any suitable growth medium. A germination medium such as MS (Murashige and Skoog), modified MS or MS+BAP (6-benzylamino purine) is particularly preferred.

The seedlings may for example be screened for symbiont-specific, e.g. fungal endophyte-specific simple sequence repeats (SSRs).

A large scale endophyte discovery program has been undertaken to establish the 'library' of fungal endophyte strains. A collection of perennial ryegrass and tall fescue accessions has been established.

The endophytes selected to inoculate the embryo may be selected utilising the techniques described in an Australian patent application filed 1 Jun. 2012 entitled "Novel Endophytes", to the present applicant, the entire disclosure of which is incorporated herein by reference. The novel endophytes described therein are particularly preferred.

Genetic analysis of endophytes in these accessions has led to the identification of a number of novel endophyte strains. These novel endophyte strains are genetically distinct from known endophyte strains. Metabolic profiling may be undertaken to determine the toxin profile of these strains.

Specific detection of endophytes in planta with SSR markers may be used to confirm the presence and identity of endophyte strains artificially inoculated into, for example, plants, plant lines, plant varieties and plant cultivars.

The inoculated germplasm may be screened by genetic analysis and/or metabolic profiling. For example, techniques of genetic analysis described in the Australian provisional patent application entitled "Novel Endophytes" may be used.

Alternatively, or in addition, the inoculated germplasm may be subjected to genetic analysis (genetically characterised) to demonstrate genetic distinction from known symbiont-genotype symbiota and to confirm the identity of symbiont, e.g. fungal endophyte, strains artificially inoculated into, for example, plants, plant lines, plant varieties and plant cultivars.

By 'genetic analysis' is meant analysing the nuclear and/or mitochondrial DNA of the symbiont such as the fungal endophyte.

This analysis may involve detecting the presence or absence of polymorphic markers, such as simple sequence repeats (SSRs) or mating-type markers. SSRs, also called microsatellites, are based on a 1-7 nucleotide core element, more typically a 1-4 nucleotide core element, that is tandemly repeated. The SSR array is embedded in complex flanking DNA sequences. Microsatellites are thought to arise due to the property of replication slippage, in which the DNA polymerase enzyme pauses and briefly slips in terms of its template, so that short adjacent sequences are repeated. Some sequence motifs are more slip-prone than others, giving rise to variations in the relative numbers of SSR loci based on different motif types. Once duplicated, the SSR array may further expand (or contract) due to further slippage and/or unequal sister chromatid exchange. The total number of SSR sites is high, such that in principle such loci are capable of providing tags for any linked gene.

SSRs are highly polymorphic due to variation in repeat number and are co-dominantly inherited. Their detection is based on the polymerase chain reaction (PCR), requiring only small amounts of DNA and suitable for automation. They are ubiquitous in eukaryotic genomes, including fungal and plant genomes, and have been found to occur every 21 to 65 kb in plant genomes. Consequently, SSRs are ideal markers for a broad range of applications such as genetic diversity analysis, genotypic identification, genome mapping, trait mapping and marker-assisted selection.

Known SSR markers which may be used to investigate endophyte diversity in perennial ryegrass are described in van Zijll de Jong et al (2003) Genome 46 (2): 277-290.

Alternatively, or in addition, the genetic analysis may involve sequencing genomic and/or mitochondrial DNA and performing sequence comparisons to assess genetic variation between symbionts such as fungal endophytes.

The symbiotum derived from the artificial seed established from the symbiont-inoculated embryo may be subjected to metabolic analysis to identify the presence of desired metabolic traits.

By 'metabolic analysis' is meant analysing metabolites, in particular toxins, produced by the symbionts, such as fungal endophytes. Preferably, this is done by generation of inoculated plants for each of the symbionts and measurement of e.g. toxin levels, resistance to pests and/or diseases, or tolerance to water and/or nutrient stress in planta. More preferably, this is done by generation of isogenically inoculated plants for each of the symbionts and measurement of toxin levels in planta.

By a 'desired genetic and metabolic profile' is meant that the symbiont such as a fungal endophyte possesses genetic and/or metabolic characteristics that result in a beneficial phenotype in an organism harbouring, or otherwise associated with, the symbiont.

Such beneficial properties include improved tolerance to water and/or nutrient stress, improved resistance to pests and/or diseases, enhanced biotic stress tolerance, enhanced drought tolerance, enhanced water use efficiency, enhanced tolerance to extremes of temperature, reduced toxicity, enhanced nutrient availability and enhanced vigour in, for example, a plant with which the symbiont is associated, relative to a control plant lacking the symbiont or containing a control symbiont such as standard toxic (ST) endophyte.

Such beneficial properties also include reduced toxicity of the associated plant to grazing animals.

For example, tolerance to water and/or nutrient stress may be increased by at least approximately 5%, more preferably at least approximately 10%, more preferably at least approximately 25%, more preferably at least approximately 50%, more preferably at least approximately 100%, relative to a control symbiont such as ST endophyte or to a no symbiont control plant. Preferably, tolerance to water and/or nutrient stress may be increased by between approximately 5% and approximately 50%, more preferably between approximately 10% and approximately 25%, relative to a control symbiont such as ST endophyte or to a no symbiont control plant.

For example, plant resistance to pests and/or diseases may be increased by at least approximately 5%, more preferably at least approximately 10%, more preferably at least approximately 25%, more preferably at least approximately 50%, more preferably at least approximately 100%, relative to a control plant. Preferably, plant resistance to diseases and/or pests may be increased by between approximately 5% and approximately 50%, more preferably between approximately 10% and approximately 25%, relative to a control plant.

For example, water use efficiency and/or plant vigour may be increased by at least approximately 5%, more preferably at least approximately 10%, more preferably at least approximately 25%, more preferably at least approximately 50%, more preferably at least approximately 100%, relative to a control symbiont such as ST endophyte or to a no symbiont control plant. Preferably, tolerance to water and/or nutrient stress may be increased by between approximately 5% and approximately 50%, more preferably between approximately 10% and approximately 25%, relative to a control symbiont such as ST endophyte or to a no symbiont control plant.

For example, toxicity may be reduced by at least approximately 5%, more preferably at least approximately 10%, more preferably at least approximately 25%, more preferably at least approximately 50%, more preferably at least approximately 100%, relative to a control symbiont such as ST endophyte or to a no symbiont control plant. Preferably, toxicity may be reduced by between approximately 5% and approximately 100%, more preferably between approximately 50% and approximately 100% relative to a control symbiont such as ST endophyte or to a no symbiont control plant.

In a preferred embodiment toxicity may be reduced to a negligible amount or substantially zero toxicity.

In a preferred embodiment, the symbiont such as a fungal endophyte may exhibit a desired toxin profile.

Preferably the endophyte is isolated from a fescue species, preferably tall fescue.

Preferably, the endophyte is of the genus *Neotyphodium*, more preferably it is from a species selected from the group consisting of *N uncinatum, N coenophialum* and *N lolii*, most preferably *N coenophialum*. The endophyte may also be from the genus *Epichloe*, including *E typhina, E baconii* and *E festucae*. The endophyte may also be of the non-*Epichloe* out-group. The endophyte may also be from a species selected from the group consisting of FaTG-3 and FaTG-3 like, and FaTG-2 and FaTG-2 like.

The endophyte may also be from the genus *Acremonium*, including *A. implicatum* and endophytes from *Brachiaria-Urochloa* grasses as described in Australian patent application No. 2011902393 entitled "Fungi and associated methods", to the present applicant, the entire disclosure of which is incorporated herein by reference.

By a 'desired toxin profile' is meant that the symbiont such as an endophyte produces significantly less toxic alkaloids, such as ergovaline or Lolitrem B, compared with a plant inoculated with a control symbiont such as standard toxic (ST) endophyte; and/or significantly more alkaloids conferring beneficial properties such as improved tolerance to water and/or nutrient stress and improved resistance to pests and/or diseases in the plant with which the symbiont is associated, such as peramine, N-formylloline, N-acetylloline and norloline, again when compared with a plant inoculated with a control symbiont such as ST or with a no symbiont control plant.

In a particularly preferred embodiment, the endophyte may be selected from the group consisting of E1, NEA10, NEA11 and NEA12, which were deposited at The National Measurement Institute, 1/153 Bertie Street, Port Melbourne, Victoria, Australia, 3207, on 5 Jan. 2010 with accession numbers V10/000001, V10/000002, V10/000003 and V10/000004, respectively, and are described in International patent application PCT/AU2011/000020, the entire disclosure of which is incorporated herein by reference. Replacement deposits were made on Apr. 15, 2016 in response to a notification of non-viability, and were assigned the same accession numbers.

In a particularly preferred embodiment, the endophyte may be selected from the group consisting of NEA16, NEA17, NEA18, NEA19, NEA20, NEA21 and NEA23, which were deposited at The National Measurement Institute, 1/153 Bertie Street, Port Melbourne, Victoria, Australia, 3207, on 3 Apr. 2012 with accession numbers V12/001413, V12/001414, V12/001415, V12/001416, V12/001417, V12/001418 and V12/001419, respectively, and are described in an Australian patent application filed 1 Jun. 2012 entitled 'Novel endophytes', to the present applicant, the entire disclosure of which is incorporated herein by reference. Replacement deposits were made on Apr. 15, 2016 in response to a notification of non-viability, and were assigned the same accession numbers.

In a particularly preferred embodiment, the endophyte may be selected from the group consisting of *Acremonium* 1.1.A (1.1A), 3.3.A (3.3A), 5.1.B (5.1B), 9.2.A (9.2A) and 12.1.A (12.1A), which were deposited at The National Measurement Institute, 1/153 Bertie Street, Port Melbourne, Victoria, Australia, 3207, on 15 Jun. 2011 with accession numbers V11/011370, V11/011371, V11/011372, V11/011373, and V11/011374, respectively, which are described in Australian patent application No. 2011902393 entitled "Fungi and associated methods", to the present applicant, the entire disclosure of which is incorporated herein by reference. Replacement deposits were made on Apr. 15, 2016 in response to a notification of non-viability, and were assigned the same accession numbers.

Such endophytes may have a desired toxin profile as hereinbefore described.

In a preferred embodiment of the present invention, the symbiont(s) such as endophyte(s) may include a genetic variation, for example, to enhance endophyte trait introgression in plants such as grasses to enhance vegetative stability of the symbiotum, intergenerational stability of the symbiotum, abiotic stress tolerance (e.g. water stress) of the symbiotum, biotic stress tolerance (e.g. disease resistance) of the symbiotum, nutrient use efficiency (e.g. phosphorus use efficiency, nitrogen use efficiency) of the symbiotum.

The genetic variation may be introduced utilizing any standard techniques, e.g. via one or more of random mutagenesis, di/poly-ploidisation, targeted mutagenesis; cisgenesis; transgenesis; intragenesis.

In a preferred embodiment, the endophyte(s) may be endophyte variants as described in an Australian patent application filed 1 Jun. 2012 entitled "Designer Endophytes", to the present applicant, the entire disclosure of which is incorporated herein by reference.

In a particularly preferred embodiment, the endophyte may be selected from the group consisting of an endophyte variant selected from the group consisting of NEA12dh5, NEA12dh6, NEA12dh13, NEA12dh14, and NEA12dh17, which were deposited at The National Measurement Institute on 3 Apr. 2012 with accession numbers V12/001408, V12/001409, V12/001410, V12/001411 and V12/001412, respectively.

Such endophytes may have a desired toxin profile as hereinbefore described.

Preferably, the organism is inoculated with the symbiont such as an endophyte by a method selected from the group consisting of infection, breeding, crossing, hybridization and combinations thereof.

In one embodiment, the plant may be inoculated by isogenic inoculation. This has the advantage that phenotypic effects of symbionts such as endophytes may be assessed in the absence of host-specific genetic effects. More particularly, multiple inoculations of endophytes may be made in plant germplasm, and regenerated plantlets transferred to soil or other growth medium.

In another embodiment, a 'library' of plant germplasm may be inoculated with multiple symbionts such as endophytes. This has the advantage of enabling favourable host-endophyte associations to be established, identified and selected ab initio.

The identification of an endophyte of the opposite mating-type that is highly compatible and stable in planta provides a means for molecular breeding of endophytes for perennial ryegrass. Preferably the plant may be infected by hyper-inoculation.

Hyphal fusion between endophyte strains of the opposite mating-type provides a means for delivery of favourable traits into the host plant, preferably via hyper-inoculation. Such strains are preferably selected from the group including an endophyte strain that exhibits the favourable characteristics of high inoculation frequency and high compatibility with a wide range of germplasm, preferably elite perennial ryegrass and/or tall fescue host germplasm and an endophyte that exhibits a low inoculation frequency and low compatibility, but has a highly favourable alkaloid toxin profile.

The symbiont-infected, e.g. endophyte-infected plants may be cultured by known techniques. The person skilled in the art can readily determine appropriate culture conditions depending on the plant to be cultured.

The screening step may include analysing plant metabolites. The metabolites may be analysed by known techniques such as chromatographic techniques or mass spectrometry, for example LCMS or HPLC. In a particularly preferred embodiment, symbiont-infected, e.g. endophyte-infected plants may be analysed by reverse phase liquid chromatography mass spectrometry (LCMS). This reverse phase method may allow analysis of specific metabolites (including lolines, peramine, ergovaline, lolitrem, and janthitrems, such as janthitrem I, janthitrem G and janthitrem F) in one LCMS chromatographic run from a single symbiont-infected plant extract.

In a particularly preferred embodiment, the endophytes may be selected from the group consisting of NEA2, NEA3, NEA6, NEA10, NEA11, NEA12, E1, NEA17, NEA21, NEA23, NEA18, NEA19, NEA16, NEA20, NEA12dh5, NEA12dh6, NEA12dh13, NEA12dh14, NEA12dh17, NEA12-DsRed and IRM1-35.

In another particularly preferred embodiment, LCMS including EIC (extracted ion chromatogram) analysis may allow detection of the alkaloid metabolites from small quantities of symbiont infected, e.g. endophyte-infected, plant material. Metabolite identity may be confirmed by comparison of retention time with that of pure toxins or extracts of endophyte-infected plants with a known toxin profile analysed under substantially the same conditions and/or by comparison of mass fragmentation patterns, for example generated.

The genetic analysis may be conducted as described above. The seedlings may for example be screened for symbiont-specific, e.g. endophyte-specific simple sequence repeats (SSRs).

Alternatively, or in addition, the seedlings may be screened for the presence of favourable symbiota via molecular phenotyping. The molecular phenotyping may be performed utilising the methods described in an Australian provisional patent application filed 1 Jun. 2012 entitled "Molecular phenotyping method", to the present applicant, the entire disclosure of which is incorporated herein by reference.

In this method seedlings may be screened for the presence of favourable symbiota via molecular phenotyping. The seedlings may, for example, be assessed for improved alkaloid production and/or improved water soluble carbohydrate:protein ratio. Such techniques may utilise an enzymatic assay, calorimetric assay, SSR markers and/or other metabolomic analysis techniques. Such analyses may be semi- or substantially automated.

Thus, the method may include screening symbiota for the presence of desirable characteristics, said method including molecular phenotyping a population of symbiota.

In a preferred embodiment, the method may include assessing the population of symbiota for alkaloid production and/or water soluble carbohydrate (WSC):protein ratio. Preferably this assessment is done using one or more methods selected from the group consisting of enzymatic assays, calorimetric assays, SSR markers and metabolomic analysis.

In a preferred embodiment, assessment of alkaloid production includes measurement of alkaloid profile and/or content in the population. Preferred alkaloids include peramine, lolitrem B and ergovaline. In a preferred embodiment, alkaloids may be inferred by SSR markers and detected by metabolomic analysis, more preferably a combination of SSR marker and metabolomic analysis are used.

In another preferred embodiment, WSC:protein ratio may be assessed. WSC may be quantified using an enzymatic assay. In a preferred embodiment, individual concentrations for sucrose, glucose, fructose and fructans may be determined. Protein may be quantified using a calorimetric assay.

In a particularly preferred embodiment, protein may be quantified by a method including:
  extracting proteins from the symbiota using an alkali, such as NaOH, preferably a weak NaOH solution;
  quantification of proteins using a colorimetric assay, such as a Bradford assay.

Detection may be carried out, for example, using a plate reader.

The symbiota may be of any suitable form, including inoculated embryos, plant seeds, germinating seeds, seedlings, plantlets, plants, etc.

Preferably the seeds are derived from symbiont-infected e.g. endophyte-infected to plants e.g. plant/endophyte symbiota.

In the method according to this aspect of the present invention, the screening step may include screening artificial seeds by accelerated ageing, which is described in an Australian patent application filed 1 Jun. 2012 entitled 'Method for selection of stable symbiota', to the present applicant, the entire disclosure of which is incorporated herein by reference.

That patent application describes a method of assessing the compatibility and/or stability of plant symbiont symbiota, such as plant/endophyte symbiota, said method including:
  providing a source of seeds including symbiont such as fungal endophyte inoculated plant embryos; and
  screening the seeds and/or their offspring for compatibility and/or stability of the plant/symbiont association (i.e. symbiota) such as plant-fungal endophyte symbiota by applying accelerated ageing thereto.

In the accelerated ageing procedure, the artificial seeds, or their offspring, may be subjected to deteriorative conditions, preferably by means of high temperature and/or increased moisture content. In a particularly preferred embodiment the seeds may be exposed to an environment of high relative humidity. For example, the seeds may be exposed to temperatures of approximately −20 to 50° C., preferably 10 to 45° C., more preferably 15 to 40° C., even more preferably 25 to 40° C. and/or to humidity levels of approximately 60% to 100%, preferably 80% to 100% for periods of e.g. approximately 1 to 30 days, preferably 2 to 10 days, more preferably 4 to 7 days.

Accelerated ageing reduces symbiont e.g. endophyte viability i.e. it allows counter-selection of unstable associations and permits the ranking of symbiota based on their stability.

Preferably the method includes the further step of subjecting the selected symbiota populations to a rapid symbiont such as fungal endophyte viability assay.

Accordingly, the method of the present invention may further include assessing the compatibility and/or stability of a plant symbiont association (i.e. symbiotum) such as plant-fungal endophyte symbiota including:
  providing a source of seeds including symbiont e.g. fungal endophyte inoculated plant embryos;
  screening the seeds and/or their offspring for compatibility and/or stability of the plant/symbiont association (i.e. symbiotum) such as plant-fungal endophyte symbiota by applying accelerated ageing thereto; and
  subjecting the selected symbiota populations to a rapid symbiont such as fungal endophyte viability assay.

The viability assay step according to this aspect of the present invention may include:
  culturing the seeds to generate plantlets, seedlings or germinating seeds;
  extracting DNA and/or RNA from the plantlets, seedlings or germinating seeds; and
  subjecting the extracted DNA and/or RNA to an assay for in planta expressed symbiont-specific gene(s), such as fungal endophyte-specific gene(s).

Preferably the seeds are derived from symbiont-inoculated plants, such as fungal endophyte-inoculated plants.

Preferably the seeds are artificial seeds, as hereinbefore described.

The seeds may be from any suitable plant. The plant may be a grass, preferably a perennial grass, legume, vine, shrub, tree, herb, flower, shrub or bush. The method according to this aspect of the present invention is particularly applicable to grasses and legumes.

The rapid endophyte viability assay is described in an Australian patent application filed 1 Jun. 2012 entitled 'Method for rapid endophyte viability assessment', to the present applicant, the entire disclosure of which is incorporated herein by reference.

Preferably the seeds are cultured for a relatively short period of time, so that a rapid assessment of symbiont viability such as fungal endophyte viability may be obtained. Preferably the seeds are cultured for approximately 1 to 10 days, more preferably 3 to 10 days, more preferably 3 to 7 days, more preferably 3 to 5 days.

Applicants have found that symbiont specific, e.g. endophyte specific, genes are expressed in this time frame, enabling early in planta symbiont viability assessment.

In a preferred form the DNA/RNA may be extracted from the leaves of seedlings, more preferably from the epicotyl, hypocotyl or similar embryonic shoot of the seedlings. In grasses, the DNA/RNA may be extracted from tillers. In another preferred form the DNA/RNA may be extracted from whole germinating seeds.

Preferably the RNA and DNA may be co-extracted, preferably in a single step. Preferably, the DNA/RNA may be extracted from 1 to 10 day-old, preferably 3 to 10 day old, more preferably 3 to 7 day old, more preferably 3 to 5 day-old epicotyls, hypocotyls or similar embryonic shoots of seedlings, in order to accelerate the process.

The assay may be an assay used to amplify and simultaneously quantify a targeted DNA/RNA molecule in the extracted DNA/RNA. Preferably the assay is a quantitative real-time polymerase chain reaction (Q-PCR/qRT-PCR) assay, or kinetic polymerase chain reaction (KPCR) assay. In a particularly preferred form, the assay may be a TaqMan or similar assay.

The symbiont specific genes such as endophyte specific genes may be of any suitable type. Preferably it is only, highly or mainly expressed in planta. Fungal endophyte genes encoding the proteins 7490, 8263, 0005 and 2232 are particularly preferred.

Primers are designed for amplification of the targeted gene(s) by methods known to those skilled in the art.

The seeds may be from any suitable plant. The plant may be a grass, preferably a perennial grass, legume, vine, shrub, tree, herb, flower, shrub or bush. The method according to this aspect of the present invention is particularly applicable to grasses and legumes.

Preferably the seeds are derived from symbiont-infected plants such as fungal endophyte-infected plants e.g. plant/endophyte symbiota.

The method according to this aspect of the present invention may further include subjecting the selected symbiota populations to phenotyping for assessment of symbiota performance and/or maintenance of desired characteristics; and selecting symbiota for poly-crossing to generate a synthetic symbiota variety, for example by polycrossing.

For example, the selected symbiota variety may be subjected to a symbiont identification assay, such as an endophyte identification assay, followed by polycrossing to generate a next generation seed. Optionally, the above steps may be repeated to confirm symbiota stability, desired characteristics, symbiont e.g. fungal endophyte identity and/or symbiont e.g. fungal endophyte incidence in the next seed generation.

Accordingly, in a further aspect of the present invention, there is provided improved symbiota including one or more plants containing one or more symbionts such as fungal endophytes produced utilising the method described above.

The plant may be a grass, tree, flower, herb, shrub or bush, vine or legume, or a product thereof.

The method steps described above may be repeated to develop later generations of symbiota seeds or plants.

In a further aspect, the present invention provides a plant, plant seed or other plant part derived from an artificial seed or symbiont-containing plant of the present invention and stably infected with a symbiont such as a fungal endophyte.

Preferably, the plant cell, plant, plant seed or other plant part is a grass, more preferably a forage, turf or bioenergy grass, such as those of the genera *Lolium* and *Festuca*, including *L. perenne* and *L. arundinaceum* and of the genera *Brachiaria* and *Urochloa*, including *B. brizantha*, *B. decumbens*, *B. humidicola* and *U. mosambicensis*.

By 'plant cell' is meant any self-propagating cell bounded by a semi-permeable membrane and containing plastid. Such a cell also required a cell wall if further propagation is desired. Plant cell, as used herein includes, without limitation, seeds suspension cultures, embryos, meristematic regions, callus tissue, leaves, roots, shoots, gametophytes, sporophytes, pollen and microspores.

As used herein, except where the context requires otherwise, the term "comprise" and variations of the term, such as "comprising", "comprises" and "comprised", are not intended to exclude further additives, components, integers or steps.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

DETAILED DESCRIPTION OF THE EMBODIMENTS

In the figures:

FIG. 1 shows artificial seeds generated through Ca-alginate coating of perennial ryegrass embryos using a coating with Ca-alginate matrix without added nutrients.

FIG. 2 shows Ca-alginate coating of perennial ryegrass embryos into artificial seeds using coating with coloured Ca-alginate matrix. Artificial seeds of perennial ryegrass coloured with Queen Green (90610); a) air-dried artificial seeds; b) artificial seeds plated on germination medium. Artificial seeds of perennial ryegrass coloured with Queen Pink (92330); c) air-dried artificial seeds; d) artificial seeds plated on germination medium.

FIG. 3 shows Ca-alginate coating of perennial ryegrass embryos into artificial seeds using coating with multiple Ca-alginate matrix layers. a) Artificial seeds of perennial ryegrass coated with first coating (non-coloured) Ca-alginate layer (layer A) with added nutrients. b) Artificial seeds of perennial ryegrass coated with two (first layer A; non-coloured plus second layer B; Queen Green-coloured) Ca-alginate layers with added nutrients; c) double-coated artificial seeds placed on germination medium.

FIG. 4 shows Ca-alginate coating of perennial ryegrass embryos into artificial seeds using coating with multiple Ca-alginate matrix layers. a)-c) Cross-sections of artificial seeds of perennial ryegrass coated with first coating (non-coloured) Ca-alginate layer (layer A) and second coating with Queen-Pink or Queen-Green coloured Ca-alginate layer (layer B). d)-e) Cross-sections of artificial seeds of perennial ryegrass coated with first coating (non-coloured) Ca-alginate layer (layer A) and second coating with Queen-Green coloured Ca-alginate layer (layer B).

FIG. 5 shows germination of seeds, embryos and artificial seeds of perennial ryegrass cv. Bronsyn E− (endophyte free, 2668 seed batch). a) Original seeds: 1% germination frequency on filter paper; b) Surface-sterilized seeds: 10% germination frequency on filter paper; c) Isolated embryos: 48% germination frequency on germination medium; d) Artificial seeds (with germination medium): 40% germination frequency on MS medium.

FIG. 6 shows germination of seeds, embryos and artificial seeds of perennial ryegrass cv. Bronsyn E+ (endophyte plus, 2667 seed batch). a) Original seeds: 10% germination frequency on filter paper; b) Surface-sterilized seeds: 30% germination frequency on filter paper; c) Isolated embryos: 90% germination frequency on germination medium; d) Artificial seeds (with germination medium): 81% germination frequency on MS medium.

Figure 1:
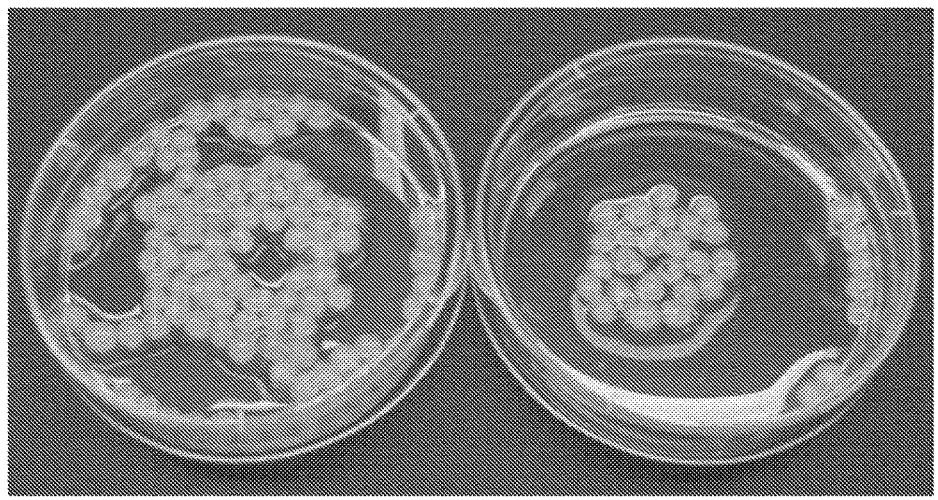

EXAMPLE 1—METHOD FOR LARGE-SCALE GENERATION OF GRASS-ENDOPHYTE SYMBIOTA (ARTIFICIAL SEEDS)

The objective of the work was to develop an efficient, robust and low-cost method for large-scale production of grass endophyte symbiota. The method should be:
a) applicable to inoculation of 10s-100s of endophyte in 100s-1000s of grass genotypes;
b) applicable to perennial ryegrass, tall fescue and *Brachiaria*; and
c) applicable to inoculation of novel and designer endophytes with de novo generated genetic variation [i.e. induced mutagenesis (ionizing radiation, colchicine), targeted mutagenesis, transgenesis, cisgenesis, intragenesis, etc.].

The method should further enable next-generation ab initio molecular breeding, selection and evaluation of grass-endophyte symbiota [rather than breeding and selection of grass host followed by endophyte inoculation and symbiota evaluation only].

The experimental strategies—and corresponding experimental steps—implemented include:
1. Large-Scale Perennial Ryegrass Seed-Derived Embryo Isolation and Artificial Seed Production
   A. Develop an efficient, low-cost, large-scale seed surface-sterilization method;
   B. Develop an efficient, low-cost, large-scale seed-derived embryo isolation method;
   C. Develop an efficient, low-cost, large-scale artificial seed production method;
   D. Test germination frequency and germination stages of artificial seeds;
   E. Assess endophyte presence in seedlings derived from artificial seeds generated with embryos isolated from endophyte-plus seeds;
2. Large-Scale Endophyte Inoculation into Perennial Ryegrass Artificial Seeds
   F. Develop an efficient, low-cost, large-scale endophyte inoculation method for artificial seeds [based on seed-derived embryo inoculation with endophyte mycelium followed by artificial seed production including double/multiple coating (inner layer plus endophyte, outer layer as 'pseudo-aleurone/endosperm') of artificial seeds]; and
   G. Assess endophyte presence in seedlings derived from artificial seeds with embryos isolated from endophyte-minus seeds inoculated with novel endophytes.

Large-Scale Perennial Ryegrass Seed-Derived Embryo Isolation and Artificial Seed Production
A) Seed Surface Sterilization Method
The seed surface sterilization method implemented includes the following steps:
Day 1: seeds were soaked in 10% sulphuric acid overnight.
Day 2: treated with 10% Domestos for 20 min and stored at 24 C after wash with distilled sterile water.
Day 3: treated with 10% Domestos for 20 min and stored at 24 C after wash with distilled sterile water, followed by embryo isolation [see B) below].

Four independent experiments were conducted with 200 seeds each.

No bacterial or fungal contamination was observed.
B) Embryo Isolation Method
Based on the successful surface-seed sterilization method [see A) above], 1,000 ryegrass seed-derived embryos can be isolated by one person within 4 hours.
Artificial Seed Production Method
Ca-Alginate Coating of Perennial Ryegrass Embryos into Artificial Seeds
i) Coating with Ca-Alginate Matrix without Added Nutrients
For the Ca-alginate coating of perennial ryegrass embryos into artificial seeds using a coating with Ca-alginate matrix without added nutrients, the following steps were undertaken:
Embryos were freshly isolated and mixed with 3% sodium alginate solution.
Alginate drops were placed into 50 mM calcium chloride solution while stirring at 60 rpm. Each drop contains one embryo.
Artificial seeds were collected after 15 min stirring and washed with sufficient distilled sterile water.
Artificial seeds were placed on germination medium MS or MS+1 mg/L BAP.

FIG. 1 shows artificial seeds generated through Ca-alginate coating of perennial ryegrass embryos using a coating with Ca-alginate matrix without added nutrients.
ii) Coating with Ca-Alginate Matrix with Added Nutrients
For the Ca-alginate coating of perennial ryegrass embryos into artificial seeds using a coating with Ca-alginate matrix with added nutrients, the following steps were undertaken:
Embryos were freshly isolated and mixed with 3% sodium alginate in modified MS medium consisting of MS (without CaCl2)+750 mg/L glutamine+5 µM $CuSO_4$+1.95 g/L MES.
Alginate drops (containing individual embryos) were placed in 50 mM calcium chloride solution while stirring at 60 rpm.
Each drop contains a single seed-derived isolated embryo.
Artificial seeds were collected after 15 min stirring and thoroughly washed with distilled sterile water.
Artificial seeds were placed on MS medium plates for germination.
iii) Coating with Coloured Ca-Alginate Matrix
For the Ca-alginate coating of perennial ryegrass embryos into artificial seeds using a coating with coloured Ca-alginate matrix with added nutrients, the following steps were undertaken:
Embryos were freshly isolated and mixed with 3% sodium alginate in modified MS medium consisting of MS (without CaCl2)+750 mg/L glutamine+5 µM $CuSO_4$+1.95 g/L MES.
Different food dyes [i.e. 10 µL/ml Queen Green (90610) or Queen Pink (92330)] were added to the sodium alginate coating solution to colour coating matrix thus establishing basis to demonstrate potential for multi-layer coating.

Alginate drops (containing individual embryos) were placed in 50 mM calcium chloride solution while stirring at 60 rpm.

Each drop, contains a single seed-derived isolated embryo.

Artificial seeds were collected after 15 min stirring and thoroughly washed with distilled sterile water.

Artificial seeds were placed on MS medium plates for germination.

Figure 2:
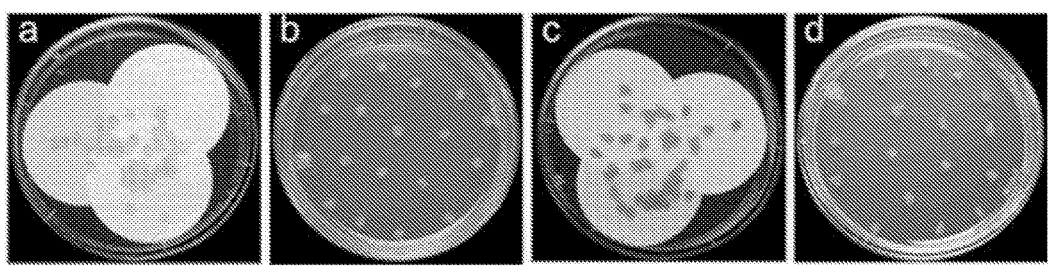

FIG. 2 shows Ca-alginate coating of perennial ryegrass embryos into artificial seeds using coating with coloured Ca-alginate matrix.

iv) Coating with Multiple Ca-Alginate Matrix Layers

For the Ca-alginate coating of perennial ryegrass embryos into artificial seeds using a coating with multiple Ca-alginate matrix layers, the following steps were undertaken:

Embryos were freshly isolated and mixed with 3% sodium alginate in modified MS medium [consisting of MS (without $CaCl_2$)+750 mg/L glutamine+5 µM $CuSO_4$+1.95 g/L MES] as the first coating layer (layer A) to make artificial seeds.

Alginate drops (containing individual embryos) were placed in 50 mM calcium chloride solution while stirring at 60 rpm. Each drop contains a single seed-derived isolated embryo.

Artificial seeds coated with layer A were collected after 15 min stirring and thoroughly washed with distilled sterile water. The average diameter of the artificial seed freshly coated with layer A is 4 mm. Artificial seeds coated with layer A were placed in Petri dish and allowed to air-dry for 1-2 hours in a laminar flow cabinet. The diameter of the air-dried artificial seed coated with layer A is 2 mm.

Air-dried artificial seeds coated with layer A were mixed with 3% sodium alginate in modified MS medium [consisting of MS (without CaCl2)+750 mg/L glutamine+5 µM $CuSO_4$+1.95 g/L MES] coloured with food dye [i.e. 10 µL/ml Queen Green (90610)] as the second coating layer (layer B) to make double-coated artificial seeds; following the same procedure.

Figure 3:
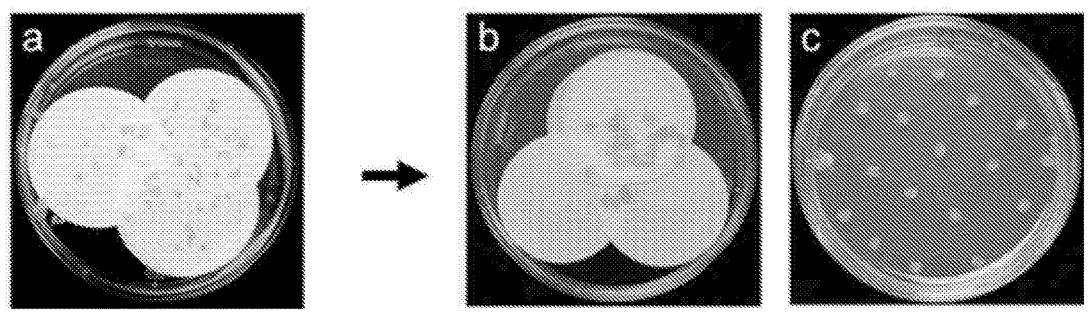

FIG. 3 shows Ca-alginate coating of perennial ryegrass embryos into artificial seeds using coating with multiple Ca-alginate matrix layers.

Figure 4:
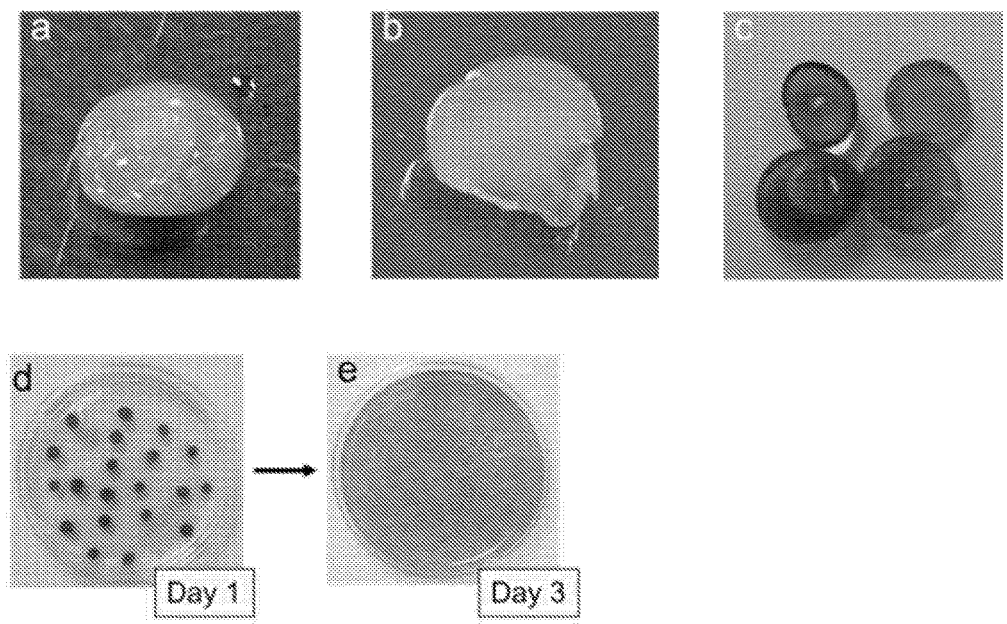

FIG. 4 shows Ca-alginate coating of perennial ryegrass embryos into artificial seeds using coating with multiple Ca-alginate matrix layers.

Freshly isolated seed-derived embryos of perennial ryegrass are individually placed in wells of a) 96-well or b) 384-well plates. With the aid of a disposable syringe sodium alginate solution is added to the individual wells and single embryos in alginate solutions are loaded in the syringe. With the aid of the syringe individual embryos coated with alginate solution are dropped into polymerising CaCl2 solution under agitation for production of artificial seeds. The use of 96-well plate is preferred over the 384 well plate for production of artificial seeds of perennial ryegrass.

Assessing Germination Frequency of Artificial Seeds

In order to assess germination frequency of artificial seeds, the following steps were undertaken:

Germination of Seeds, Embryos and Artificial Seeds of Perennial Ryegrass Cv. Bronsyn E⁻ (Endophyte Free, 2668 Seed Batch)

Figure 5:
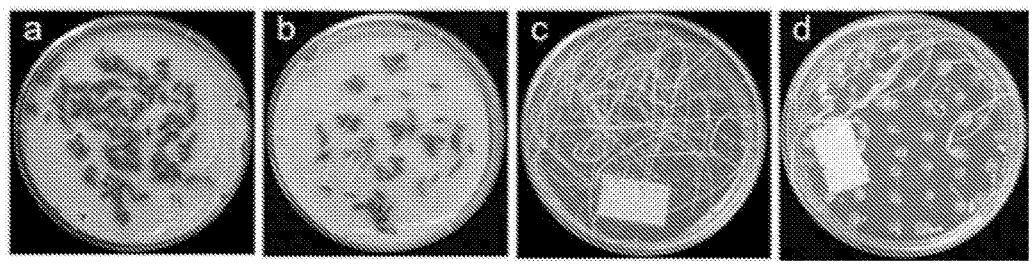

Seed germination frequency was comparatively assessed for (FIG. 5):

a) Original seeds: 1% germination frequency on filter paper;

b) Surface-sterilized seeds: 10% germination frequency on filter paper;

c) Isolated embryos: 48% germination frequency on germination medium;

d) Artificial seeds (with germination medium): 40% germination frequency on MS medium.

Germination of Seeds, Embryos and Artificial Seeds of Perennial Ryegrass Cv. Bronsyn E+(Endophyte Plus, 2667 Seed Batch)

Figure 6:
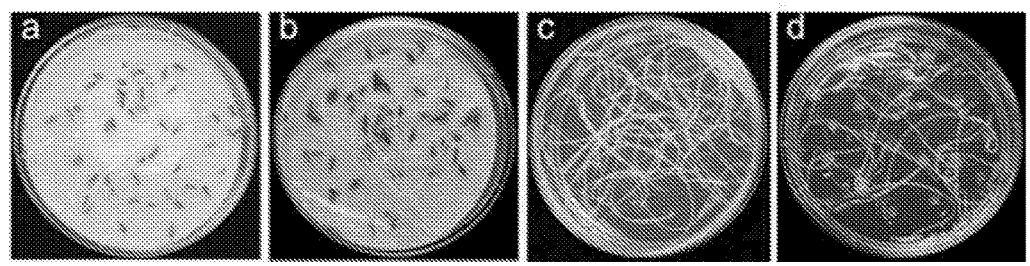

Seed germination frequency was comparatively assessed for (FIG. 6):

a) Original seeds: 10% germination frequency on filter paper;

b) Surface-sterilized seeds: 30% germination frequency on filter paper;

c) Isolated embryos: 90% germination frequency on germination medium;

d) Artificial seeds (with germination medium): 81% germination frequency on MS medium.

Figure 7:
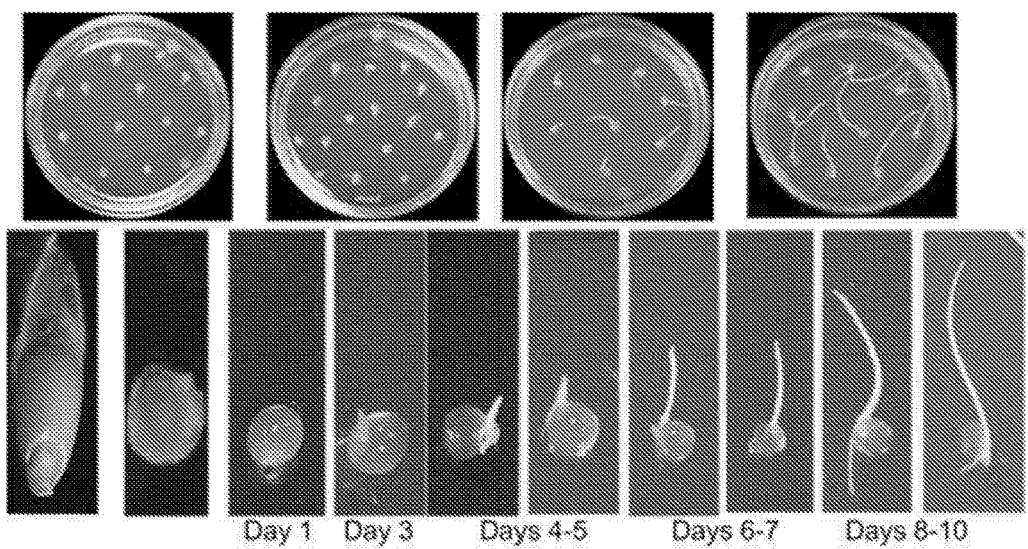
FIG. 7 shows germination of artificial seeds and development of artificial-seed derived seedlings in perennial ryegrass.

FIG. 7 shows germination of artificial seeds and development of artificial-seed derived seedlings in perennial ryegrass.

Assessing Endophyte Presence in Seedlings Derived from Artificial Seeds

In order to assess endophyte presence in seedlings derived from artificial seeds, the following experiments were undertaken:

Endophyte Presence in Seedlings Derived from Seeds and Artificial Seeds of Perennial Ryegrass Seed Cv. Bronsyn E+(Endophyte Plus, 2667 Seed Batch)

Twenty seedlings of Bronsyn E+(2667) seeds germinated on filter paper were transferred to soil.

Twenty five seedlings from germinated artificial seeds generated with Bronsyn E plus (2667) seed-derived embryos were transferred to soil. The embryos in artificial seeds were sterilized using 10% $H_2SO_4$ overnight treatment.

Following 6 week grow-out of seedlings derived from seeds and artificial seeds, endophyte presence was assessed based on endophyte-specific SSR test.

Twenty seedlings of Bronsyn E plus (2667; containing ST endophyte) seeds germinated on filter paper were transferred to soil, leading to 13 of 19 seedlings (68%) testing positive for ST endophyte presence in the endophyte-specific SSR test.

Twenty five seedlings from germinated artificial seeds generated with Bronsyn E plus (2667) seed-derived embryos were transferred to soil. The embryos in artificial seeds were sterilized using 10% $H_2SO_4$ overnight treatment, leading to 19 of 23 seedlings (83%) testing positive for ST endophyte in the endophyte-specific SSR test, clearly indicating that the methods for seed surface sterilization, large-scale embryo isolation, and artificial seed production with Ca-alginate coating do not negatively affect viability of a resident endophyte.

Large-Scale Inoculation of Endophytes in Perennial Ryegrass Artificial Seeds

Figure 8:
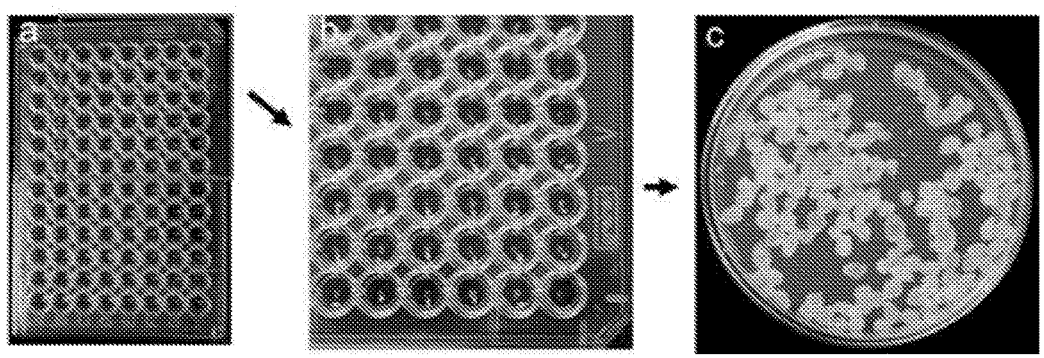
FIG. 8 shows freshly isolated seed-derived embryos of perennial ryegrass individually placed in wells of a) 96-well and b) endophyte mycelium suspension added to individual wells and allowed to partly air-dry under laminar flow prior to c) production of artificial seeds coated with Ca-alginate layer.

Different methods for the large-scale inoculation of endophytes in perennial ryegrass artificial seeds were developed, with examples of methods 1 to 3 described below:

Inoculation of Isolated Seed-Derived Embryos with Endophyte Mycelium and Production of Endophyte-Infected Artificial Seeds in Perennial Ryegrass Freshly isolated seed-derived embryos of perennial ryegrass are individually placed in wells of a) 96-well and b) endophyte mycelium suspension added to individual wells and allowed to partly air-dry under laminar flow prior to c) production of artificial seeds coated with Ca-alginate layer (FIG. 8).

Method 1: Direct Inoculation of Isolated Embryos with Endophyte Suspension Prior to Ca-Alginate Coating Method 1, inoculation of isolated seed-derived embryos with endophyte mycelium and production of endophyte-infected artificial seeds in perennial ryegrass, is based on direct inoculation of isolated embryos with endophyte suspension prior to Ca-alginate coating as follows:

Freshly isolated embryos of perennial ryegrass are incubated with endophyte suspension (1/16 dilution) for 30 mins at RT in individual wells of 96-well plates.

Inoculation suspension is removed from well and inoculated embryos are allowed to partly air-dry on filter paper disks.

Figure 9:
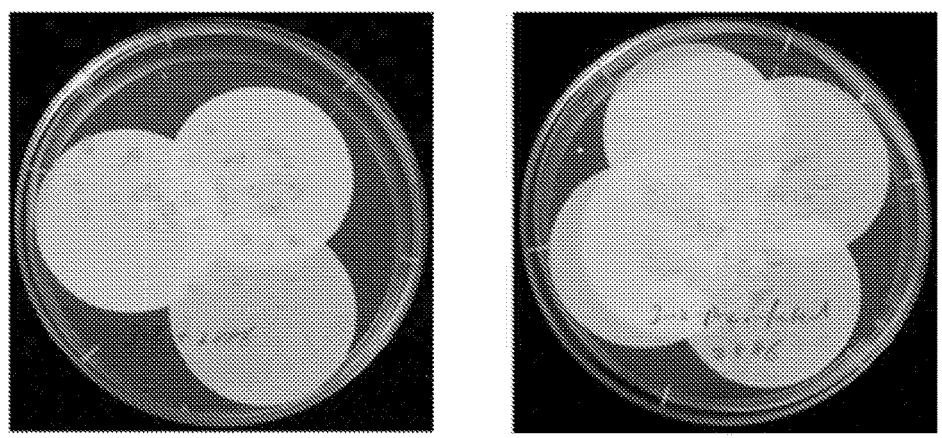
FIG. 9 shows artificial seeds produced by method 1.

Artificial seeds are produced (FIG. 9) with endophyte-inoculated embryos with 3% sodium alginate-containing modified MS growth medium [MS (without $CaCl_2$)+750 mg/L glutamine+5 µM $CuSO_4$+1.95 g MES+1 mg/l BAP].

Artificial seeds are allowed to germinate on MS medium for germination.

Freshly isolated embryos of perennial ryegrass are directly inoculated with endophyte suspension (1/8 dilution), partly air-dried and then coated with Ca-m alginate in individual wells of 96-well plates.

Figure 10:
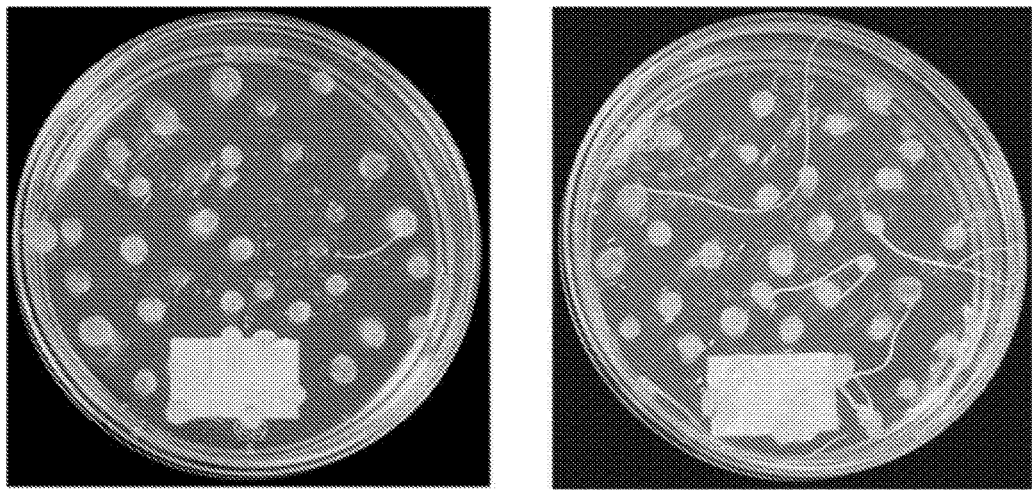
FIG. 10 shows germinating artificial seeds produced by method 1.

Artificial seeds from perennial ryegrass directly inoculated with endophyte and then coated with Ca-alginate layer are able to germinate on MS germination medium (FIG. 10).

Method 2: Direct Coating of Isolated Embryos with Endophyte-Containing Ca-Alginate Layer Method 2, inoculation of isolated seed-derived embryos with endophyte mycelium and production of endophyte-infected artificial seeds in perennial ryegrass, is based on direct coating of isolated embryos with endophyte-containing Ca-alginate layer as follows:

Embryos of perennial ryegrass are freshly isolated in endophyte suspension (1/16 dilution) in individual wells of 96-well plates.

Two-fold concentration sodium alginate (6%) modified MS medium [MS (without $CaCl_2$)+750 mg/L glutamine+5 µM $CuSO_4$+1.95 g MES+1 mg/l BAP] is added to the individual wells to coat embryos with an endophyte-containing alginate layer.

Figure 11:
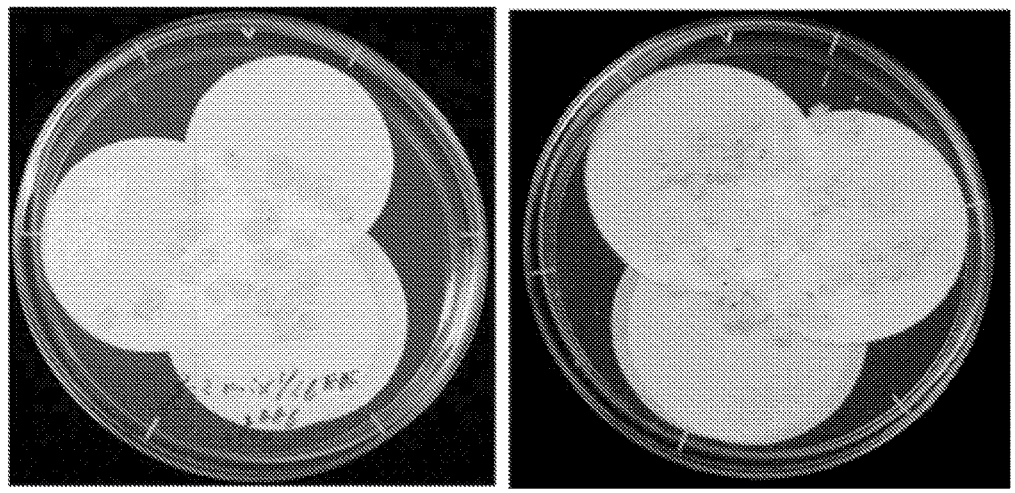
FIG. 11 shows artificial seeds produced by method 2.

Artificial seeds are produced with endophyte-layer coated embryos (FIG. 11).

Artificial seeds are allowed to germinate on MS medium for germination.

Embryos of perennial ryegrass are freshly isolated and coated with endophyte suspension (1/8 or 1/16 dilutions) with Ca-alginate then added to generate an endophyte-containing alginate layer coating the embryos in individual wells of 96-well plates.

Figure 12:
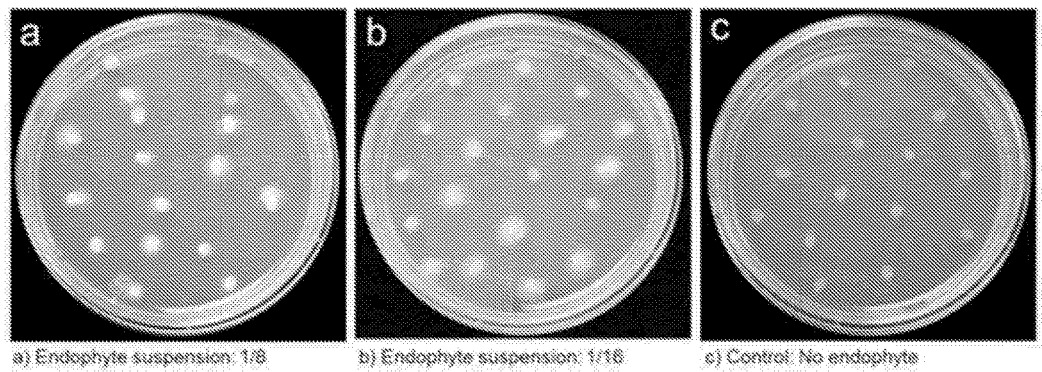
FIG. 12 shows artificial seeds produced by method 2 with endophyte outgrowth.

Following culture, endophyte out-growth is observed from the endophyte-containing alginate layer used to coat the isolated embryos of perennial ryegrass (irrespectively of endophyte suspension dilution rate used; FIG. 12) demonstrating viability of the endophyte included in the Ca-alginate coating layer.

Method 3: Double-Coating of Artificial Seeds Generated from Endophyte Inoculated Isolated Embryos Method 3, inoculation of isolated seed-derived embryos with endophyte mycelium and production of endophyte-infected artificial seeds in perennial ryegrass, is based on double-coating of artificial seeds generated from endophyte-inoculated isolated embryos as follows:

Freshly isolated embryos of perennial ryegrass are coated with an endophyte suspension (1/16 dilution), mixed with alginate [6% Ca-alginate in modified MS medium (without $CaCl_2$)+750 mg/L glutamine+5 µM $CuSO_4$+1.95 g MES+1 mg/l BAP] to generate a first coating layer containing endophytes in individual wells of 96-well plates.

Artificial seeds with a first endophyte-containing alginate layer coating freshly isolated embryos of perennial ryegrass are blot-dried on filter paper in laminar air flow for 30 mins and then coated with a second alginate layer of 3% Ca-alginate without any nutrients, Double-coated artificial seeds with endophyte-containing layer coated embryos of perennial ryegrass are then germinated on MS medium.

Figure 13:
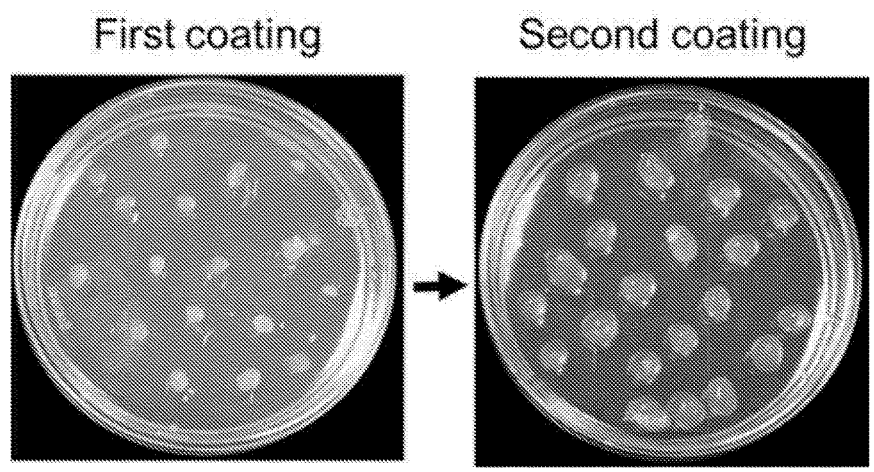
FIG. 13 shows artificial seeds produced by method 3.

Second coating with nutrient deprived medium of endophyte-inoculated artificial seeds aims to reduce endophyte out-growth during germination and restrict endophyte growth in close proximity to isolated perennial ryegrass embryo (FIG. 13).

Artificial seeds with a first endophyte-containing alginate layer coating freshly isolated embryos of perennial ryegrass are blot-dried on filter paper in laminar air flow for 30 mins and then coated with a second alginate layer of 3% Ca-alginate without any nutrients.

Figure 14:
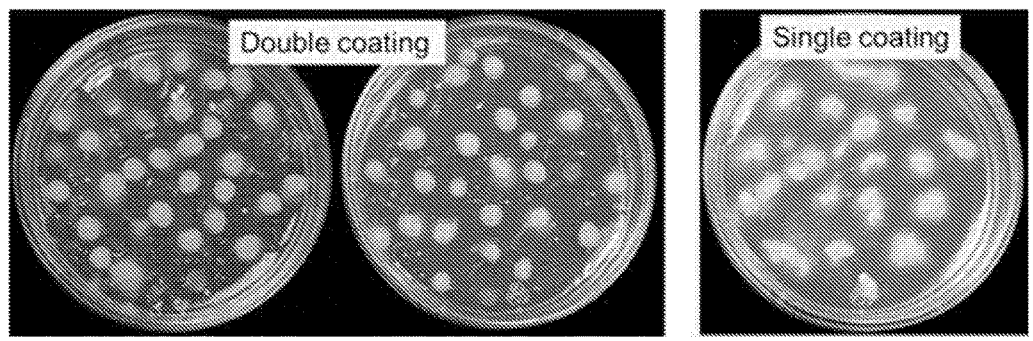
FIG. 14 shows artificial seeds produced by method 3 with endophyte outgrowth.

Endophyte growth is mainly restricted to inner alginate coating layer for a period of up to 3 weeks (FIG. 14).

Embryos of perennial ryegrass are freshly isolated directly in endophyte suspension (1/8 dilution), then partly air-died and coated with a first alginate layer [3% Ca-alginate in modified MS medium (without $CaCl_2$)+750 mg/L glutamine+5 µM $CuSO_4$+1.95 g MES+1 mg/l BAP] in individual wells of 96-well plates.

Artificial seeds with directly endophyte-inoculated embryos of perennial ryegrass are stored at 4 C overnight and then coated with a second alginate layer of 3% Ca-alginate without any nutrients.

Double-coated artificial seeds with directly endophyte-inoculated embryos of perennial ryegrass are then germinated on MS medium.

Figure 15:
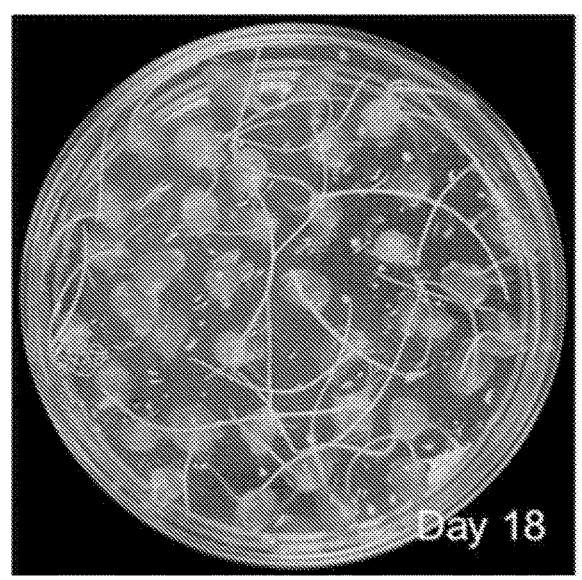
FIG. 15 shows germinating artificial seeds produced by method 3.

Double-coated artificial seeds with directly endophyte-inoculated embryos of perennial ryegrass germinated on MS medium show germination rates comparable to the original seed batch used for embryo isolation (FIG. 15).

Assessing Endophyte Presence in Seedlings Derived from Artificial Seeds with Seed-Derived Embryos Inoculated with Novel Endophytes In order to assess endophyte presence in seedlings derived from artificial seeds with seed-derived embryos inoculated with novel endophytes (e.g. NEA11) using Method 1, the following experiment was undertaken:

Endophyte Presence in Seedlings Derived from Artificial Seeds Produced with Embryos from Perennial Ryegrass Seed Cv. Bronsyn E– (Endophyte Minus, 2668 Seed Batch) Inoculated with Novel Endophyte NEA11

Following 6 week grow-out of seedlings derived from artificial seeds, endophyte presence was assessed based on endophyte-specific SSR test.

Twenty-three seedlings from germinated artificial seeds generated with Bronsyn E minus (2668) seed-derived embryos inoculated with NEA11 using Method 1 were transferred to soil. 6 of 23 seedlings (i.e. 26%) tested positive for NEA11 endophyte presence in the endophyte-specific SSR test demonstrating the establishment of symbiota (Table 1). Endophyte presence in symbiota established from germinated artificial seeds generated with perennial ryegrass seed-derived embryos inoculated with novel endophyte NEA11 using Method 1 was confirmed following 3 months after transfer to soil.

TABLE 1

Assessing Endophyte Presence in Seedlings Derived from Artificial Seeds with Seed-Derived Embryos Inoculated with Novel Endophytes

| | SSR Marker | | | | | | Endophyte |
|---|---|---|---|---|---|---|---|
| | NLESTA1QA09 | | NLESTA1NG03 | | NLESTA1CC05 | | |
| Seedling | Allele 1 | Allele 2 | Allele 1 | Allele 2 | Allele 1 | Allele 2 | detected |
| 2668_4 | 153 | 184 | 226 | | 167 | | NEA11 |
| 2668_15 | 153 | 184 | 226 | | 167 | | NEA11 |
| 2668_1 | 153 | 184 | 226 | | 167 | | NEA11 |
| 2_2 | 153 | 184 | 226 | | 167 | | NEA11 |
| 2668 Bb1 | 153 | 184 | 226 | | 167 | | NEA11 |
| 2668_13 | 153 | 184 | 226 | | 167 | | NEA11 |

Large-Scale Inoculation of Designer Endophytes in Perennial Ryegrass Artificial Seeds Large-scale inoculation of designer endophytes derived from induced mutagenesis through colchicine-treatment (e.g. NEA12dh17) or derived from X-ray mutagenesis (e.g. IRM1-35) in perennial ryegrass artificial seeds is carried out using methods 1 to 3 described above.

Freshly isolated embryos of perennial ryegrass are incubated with designer endophyte (e.g. NEA12dh17, IRM1-35) suspension (1/16 dilution) for 30 mins at RT in individual wells of 96-well plates.

Inoculation suspension is removed from well and inoculated embryos are allowed to partly air-dry on filter paper disks.

Artificial seeds are produced with designer endophyte-inoculated embryos with 3% sodium alginate-containing modified MS growth medium [MS (without $CaCl_2$)+750 mg/L glutamine+5 µM $CuSO_4$+1.95 g MES+1 mg/l BAP].

Artificial seeds are allowed to germinate on MS medium for germination.

Freshly isolated embryos of perennial ryegrass are directly inoculated with designer endophyte (e.g. NEA12dh17, IRM1-35) suspension (1/8 dilution), partly air-dried and then coated with Ca-alginate in individual wells of 96-well plates.

Artificial seeds from perennial ryegrass directly inoculated with designer endophytes (e.g. NEA12dh17, IRM1-35) and then coated with Ca-alginate layer are able to germinate on MS germination medium leading to the establishment of symbiota. Designer endophyte presence and identity in the symbiota generated following large-scale inoculation of designer endophytes derived from induced mutagenesis through colchicine-treatment (e.g. NEA12dh17) or derived from X-ray mutagenesis (e.g. IRM1-35) in perennial ryegrass artificial seeds is demonstrated using an endophyte-specific SSR test.

Large-Scale Inoculation of Transgenic Endophytes in Perennial Ryegrass Artificial Seeds Large-scale inoculation of transgenic endophytes derived from genetic transformation of NEA12 endophyte with plasmid containing a chimeric gene for expression of the DsRed fluorescent marker gene (e.g. NEA12-DsRed) in perennial ryegrass artificial seeds is carried out using method 1 described above.

Freshly isolated embryos of perennial ryegrass are incubated with transgenic endophyte (e.g. NEA12-DsRed) suspension (1/16 dilution) for 30 mins at RT in individual wells of 96-well plates.

Inoculation suspension is removed from well and inoculated embryos are allowed to partly air-dry on filter paper disks.

Artificial seeds are produced with transgenic endophyte-inoculated embryos with 3% sodium alginate-containing modified MS growth medium [MS (without $CaCl_2$)+750 mg/L glutamine+5 µM $CuSO_4$+1.95 g MES+1 mg/l BAP].

Artificial seeds are allowed to germinate on MS medium for germination.

Freshly isolated embryos of perennial ryegrass are directly inoculated with transgenic endophyte (e.g. NEA12-DsRed) suspension (1/8 dilution), partly air-dried and then coated with Ca-alginate in individual wells of 96-well plates.

Artificial seeds from perennial ryegrass directly inoculated with transgenic endophyte (e.g. NEA12-DsRed) and then coated with Ca-alginate layer are able to germinate on MS germination medium leading to the establishment of symbiota with transgenic endophytes. Transgenic endophyte presence and identity in the symbiota generated following large-scale inoculation of transgenic endophyte (e.g. NEA12-DsRed) in perennial ryegrass artificial seeds is demonstrated using an endophyte-specific SSR and transgene-specific PCR test.

Large-Scale Inoculation of Novel Endophytes in Tall Fescue Artificial Seeds

Large-scale inoculation of novel endophytes from tall fescue (e.g. NEA17, NEA19, NEA20) in tall fescue artificial seeds is carried out using method 1 described above.

Freshly isolated embryos of tall fescue are incubated with novel fescue endophytes (e.g. NEA17, NEA19, NEA20) suspension (1/16 dilution) for 30 mins at RT in individual wells of 96-well plates.

Inoculation suspension is removed from well and inoculated embryos are allowed to partly air-dry on filter paper disks.

Artificial seeds are produced with novel endophyte-inoculated embryos with 3% sodium alginate-containing modified MS growth medium [MS (without $CaCl_2$)+750 mg/L glutamine+5 µM $CuSO_4$+1.95 g MES+1 mg/l BAP].

Artificial seeds are allowed to germinate on MS medium for germination.

Freshly isolated embryos of tall fescue are directly inoculated with novel fescue endophytes (e.g. NEA17, NEA19, NEA20) suspension (1/8 dilution), partly air-dried and then coated with Ca-alginate in individual wells of 96-well plates.

Artificial seeds from tall fescue directly inoculated with novel fescue endophytes (e.g. NEA17, NEA19, NEA20) and then coated with Ca-alginate layer are able to germinate on MS germination medium leading to the establishment of symbiota. Novel endophyte presence and identity in the symbiota generated following large-scale inoculation of novel fescue endophytes (e.g. NEA17, NEA19, NEA20) in tall fescue artificial seeds are demonstrated using an endophyte-specific SSR test.

EXAMPLE 2—ENDOPHYTE INOCULATION METHOD IN PERENNIAL RYEGRASS

This example describes enhancement of endophyte inoculation frequency following puncturing isolated embryos of perennial ryegrass with an hypodermic needle prior to inoculation using method 1 (direct inoculation) or method 2 (coating with endophyte containing Ca-alginate layer).

Figure 16:
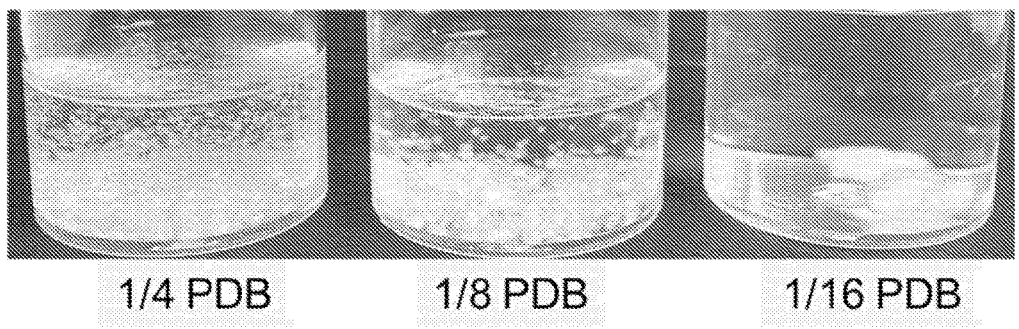
FIG. 16 shows endophyte suspensions at different dilution rates.

Embryos isolated from perennial ryegrass seeds were inoculated with endophyte NEA11 using either methods 1 or 2, with endophyte suspensions at different dilution rates (1/4, 1/8, 1/16; see FIG. 16) subjected, with and without wounding of embryos with a hypodermic needle. Puncturing of embryos prior to inoculation greatly enhanced inoculation efficiency, demonstrated by SSR-based endophyte detection in 6 week old symbiota recovered from artificial seeds derived from inoculated embryos (see Table 2).

EXAMPLE 3—ENDOPHYTE INOCULATION METHOD IN PERENNIAL RYEGRASS AND TALL FESCUE

This example describes enhancement of endophyte inoculation frequency following puncturing isolated embryos of perennial ryegrass (*L. perenne*) and tall fescue (*F. arundinacea*) with an hypodermic needle prior to inoculation using method 1 (direct inoculation) or method 2 (coating with endophyte containing Ca-alginate layer).

Method 1: Direct Inoculation of Isolated Embryos with Endophyte Suspension Prior to Ca-Alginate Coating Method 2: Direct Coating of Isolated Embryos with Endophyte-Containing Ca-Alginate Layer Embryos isolated from seeds from different varieties were inoculated with different endophytes (NEA11 and NEA17) using either methods 1 or 2, with and without wounding of embryos with hypodermic needle. Puncturing of embryos prior to inoculation greatly enhanced inoculation efficiency, demonstrated by SSR-based endophyte detection in 6 week-old symbiota recovered from artificial seeds derived from inoculated embryos (see Table 3).

TABLE 3

Number and frequency of endophyte-inoculated perennial ryegrass and tall fescue plants recovered following different endophyte inoculation treatment methods

| | | | | No. of artificial seeds Method 1 | | | No. of artificial seeds Method 1 plus wounding | | |
|---|---|---|---|---|---|---|---|---|---|
| Species | Variety | Experiment | Endophyte | Total | Negative | Positive | Total | Negative | Positive |
| *L. perenne* | Alto | 1 | NEA11 (LpTG-2) | 42 | 42 | 0 | 20 | 16 | 4 |
| | | 2 | NEA11 (LpTG-2) | 21 | 21 | 0 | 21 | 20 | 1 |
| | | 3 | NEA11 (LpTG-2) | 84 | 84 | 0 | 40 | 29 | 11 |
| *F. arundinacea* | Dovey | 1 | NEA11 (LpTG-2) | 42 | 42 | 0 | 40 | 39 | 1 |
| *L. perenne* | Alto | 1 | NEA17 (FaTG-2) | 42 | 42 | 0 | 42 | 42 | 0 |
| *F. arundinacea* | Dovey | 1 | NEA17 (FaTG-2) | 70 | 70 | 0 | 35 | 35 | 0 |
| | Finesse | 2 | NEA17 (FaTG-2) | 42 | 42 | 0 | 70 | 70 | 0 |

| | | | | No. of artificial seeds Method 2 | | | No. of artificial seeds Method 2 plus wounding | | |
|---|---|---|---|---|---|---|---|---|---|
| Species | Variety | Experiment | Endophyte | Total | Negative | Positive | Total | Negative | Positive |
| *L. perenne* | Alto | 1 | NEA11 (LpTG-2) | 84 | 84 | 0 | 18 | 9 | 9 |

TABLE 2

Number and frequency of endophyte-inoculated perennial ryegrass plants recovered following different endophyte inoculation treatment methods

| | | PDB | | Endophyte Detected | | |
|---|---|---|---|---|---|---|
| Treatment | Method | conc | Wounding | NEA11 | E- | Inoculation % |
| A | 1 | 1/16 | No | 0 | 42 | 0 |
| B | 1 | 1/8 | No | 0 | 42 | 0 |
| C | 1 | 1/8 | Puncture | 11 | 29 | 27.5 |
| D | 2 | 1/16 | No | 0 | 42 | 0 |
| E | 2 | 1/8 | No | 0 | 42 | 0 |
| F | 2 | 1/8 | Puncture | 9 | 9 | 50 |

Method 1: Direct Inoculation of Isolated Embryos with Endophyte Suspension Prior to Ca-Alginate Coating
Method 2: Direct Coating of Isolated Embryos with Endophyte-Containing Ca-Alginate Layer The claims defining the invention are as follows:

1. An artificial seed, comprising:
   a plant embryo inoculated with one or more symbionts and subsequently coated with a first coating to encapsulate the embryo.

2. The artificial seed according to claim 1, wherein said artificial seed is further coated with a second coating layer.

3. The artificial seed according to claim 2, wherein said second coating layer includes added nutrients.

4. The artificial seed according to claim 2, wherein said second coating layer is a nutrient deprived layer.

5. The artificial seed according to claim 1, wherein the embryo is from a plant selected from the group consisting of grasses and legumes.

6. The artificial seed according to claim 1, wherein the symbiont is a fungal endophyte.

7. The artificial seed according to claim 1, wherein the embryo is treated to create one or more points of entry for the symbiont.

8. The artificial seed according to claim 1, wherein the first coating comprises calcium alginate.

\* \* \* \* \*

UNITED STATES PATENT AND TRADEMARK OFFICE
CERTIFICATE OF CORRECTION

PATENT NO. : 10,051,777 B2
APPLICATION NO. : 14/404856
DATED : August 21, 2018
INVENTOR(S) : Spangenberg et al.

Page 1 of 1

It is certified that error appears in the above-identified patent and that said Letters Patent is hereby corrected as shown below:

In the Specification

Column 7, Lines 1-4 should read: ... Replacement deposits were made on Apr. 15, 2016 in response to a notification of non-viability, and were assigned the same accession numbers. A replacement deposit of NEA12, Accession No. V10/000004, was deposited with The National Measurement Institute, 1/153 Bertie Street, Port Melbourne, Victoria, Australia, 3207 on September 3, 2019. This replacement deposit of NEA12 was assigned the same accession number, V10/000004.

Signed and Sealed this
Third Day of March, 2020

Andrei Iancu
*Director of the United States Patent and Trademark Office*